(12) United States Patent
Fogarty

(10) Patent No.: US 8,066,926 B2
(45) Date of Patent: Nov. 29, 2011

(54) METHOD OF MANUFACTURING REINFORCED MEDICAL TUBING

(76) Inventor: Terence M. Fogarty, Hudson, WI (US)

( * ) Notice: Subject to any disclaimer, the term of this patent is extended or adjusted under 35 U.S.C. 154(b) by 270 days.

(21) Appl. No.: 12/276,752

(22) Filed: Nov. 24, 2008

(65) Prior Publication Data

US 2009/0236770 A1  Sep. 24, 2009

Related U.S. Application Data

(60) Provisional application No. 61/038,206, filed on Mar. 20, 2008.

(51) Int. Cl.
*B28B 21/00* (2006.01)

(52) U.S. Cl. ........ 264/255; 264/250; 264/251; 264/259; 264/271.1; 264/275; 264/277; 264/278; 264/505; 264/506

(58) Field of Classification Search ............... 264/505, 264/506, 250, 251, 255, 259, 271.1, 275, 264/277, 278; 138/144, 150, 153
See application file for complete search history.

(56) References Cited

U.S. PATENT DOCUMENTS

| | | | | |
|---|---|---|---|---|
| 3,076,737 A * | 2/1963 | Roberts | .......................... | 264/506 |
| 4,113,820 A * | 9/1978 | Tamborini et al. | ......... | 264/171.2 |
| 4,196,031 A * | 4/1980 | Lalikos et al. | ................ | 138/144 |
| 4,484,586 A | 11/1984 | McMickle et al. | | |
| 4,764,324 A * | 8/1988 | Burnham | ....................... | 264/103 |
| 4,872,396 A * | 10/1989 | Wimbush | ...................... | 264/274 |
| 5,004,574 A * | 4/1991 | Sandt | ............................. | 264/277 |
| 5,957,785 A * | 9/1999 | Masutani et al. | ............. | 473/377 |
| 6,053,891 A | 4/2000 | DeCampli | | |
| 6,213,995 B1 | 4/2001 | Steen et al. | | |
| 6,315,715 B1 * | 11/2001 | Taylor et al. | ................... | 600/140 |
| 6,563,045 B2 | 5/2003 | Goett et al. | | |
| 7,216,675 B2 | 5/2007 | Wisdom et al. | | |
| 2001/0016728 A1 | 8/2001 | Kelley | | |
| 2002/0132076 A1* | 9/2002 | Stevens | ........................ | 428/35.8 |
| 2003/0166777 A1 | 9/2003 | Vachon | | |
| 2005/0161101 A1 | 7/2005 | Wisdom et al. | | |
| 2005/0165366 A1 | 7/2005 | Brustad et al. | | |
| 2005/0196570 A1* | 9/2005 | Lindsay | ........................ | 156/143 |
| 2007/0049903 A1 | 3/2007 | Jansen et al. | | |

* cited by examiner

*Primary Examiner* — Joseph Del Sole
*Assistant Examiner* — Timothy Kennedy
(74) *Attorney, Agent, or Firm* — Allen J. Oh

(57) ABSTRACT

Methods for manufacturing reinforced tubing suitable for medical device applications are disclosed. An inner layer is molded around a core to define an inner surface adjacent to the core and an outer surface opposite the inner surface. The outer surface includes one or more recessed pathways defined therein. A reinforcement member is then formed in each of the one or more recessed pathways of the molded inner layer. An outer layer including an inner surface and an outer surface is subsequently molded over the inner layer and the reinforcement member. The inner surface of the outer layer substantially conforms to the outer surface of the inner layer and the reinforcement member. The core is then removed from within the inner layer to provide a lumen through the inner layer.

16 Claims, 12 Drawing Sheets

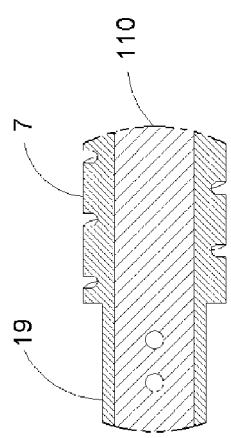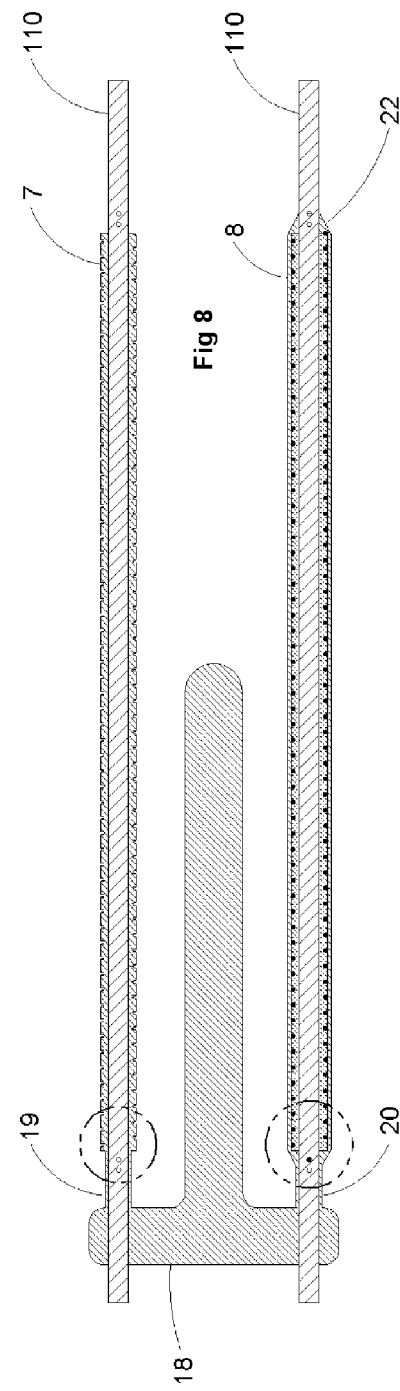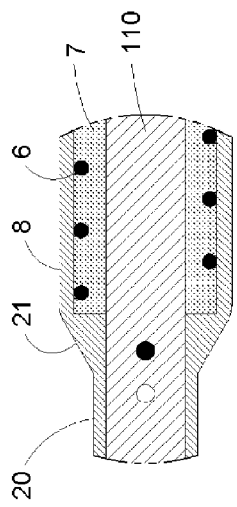

METHOD OF MANUFACTURING REINFORCED MEDICAL TUBING

CROSS-REFERENCE TO RELATED APPLICATION

This application claims the benefit of provisional application Ser. No. 61/038,206, filed Mar. 20, 2008, entitled "REINFORCED MEDICAL TUBING AND METHOD TO MANUFACTURE," which is incorporated by reference in its entirety. This application is related to co-pending application Serial No. 12/276,761, filed on even date herewith, entitled "Reinforced Medical Tubing."

TECHNICAL FIELD

The present invention relates to medical devices. In particular, the present invention relates to a reinforced tubing suitable for connecting components in medical devices.

BACKGROUND

In certain implantable devices, flexible silicone tubing is used to provide a fluid conduit between and connect device components. One such implantable device is a multi-component inflatable penile prosthesis (IPP). In the early 1980's, spiral reinforcement was incorporated in silicone tubing for IPP to provide kink-resistance. Historically, spiral reinforced silicone tubing is fabricated by first extruding and curing an inner layer of silicone elastomer over a core material, wrapping the inner layer of silicone with spiral reinforcement, extruding and curing an outer layer of silicone elastomer over the spiral reinforced inner layer, cutting the tubing and core material to desired lengths, and separating the tubing from the core material.

SUMMARY

The present invention relates to methods for manufacturing reinforced tubing suitable for medical device applications. In one embodiment, an inner layer is molded around a core to define an inner surface adjacent to the core and an outer surface opposite the inner surface. The outer surface includes one or more recessed pathways defined therein. A reinforcement member is then formed in each of the one or more recessed pathways of the molded inner layer. An outer layer including an inner surface and an outer surface is subsequently molded over the inner layer and the reinforcement member. The inner surface of the outer layer substantially conforms to the outer surface of the inner layer and the reinforcement member. The core is then removed from within the inner layer to provide a lumen through the inner layer.

In another embodiment, an inner layer with a recessed pathway is molded over a core material using inner layer mold cavity halves. The molded inner layer and core are then removed from the inner layer mold cavity halves, a reinforcement member is formed in the recessed pathway of the inner layer, and ends of the reinforcement member are secured to the core. An outer layer is then molded over the inner layer and the reinforcement member in outer layer mold cavity halves. After the outer layer, inner layer, and reinforcement member are removed from the outer layer mold cavity halves, the core is removed from within the inner layer to provide a lumen through the inner layer.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 8 is a cross-sectional view of the molded shot with inner and outer tubing layers shown in FIG. 7.

FIGS. 8a and 8b are enlarged cross-sectional views of portions of the molded shot shown in FIG. 8.

DETAILED DESCRIPTION

Figure 1:
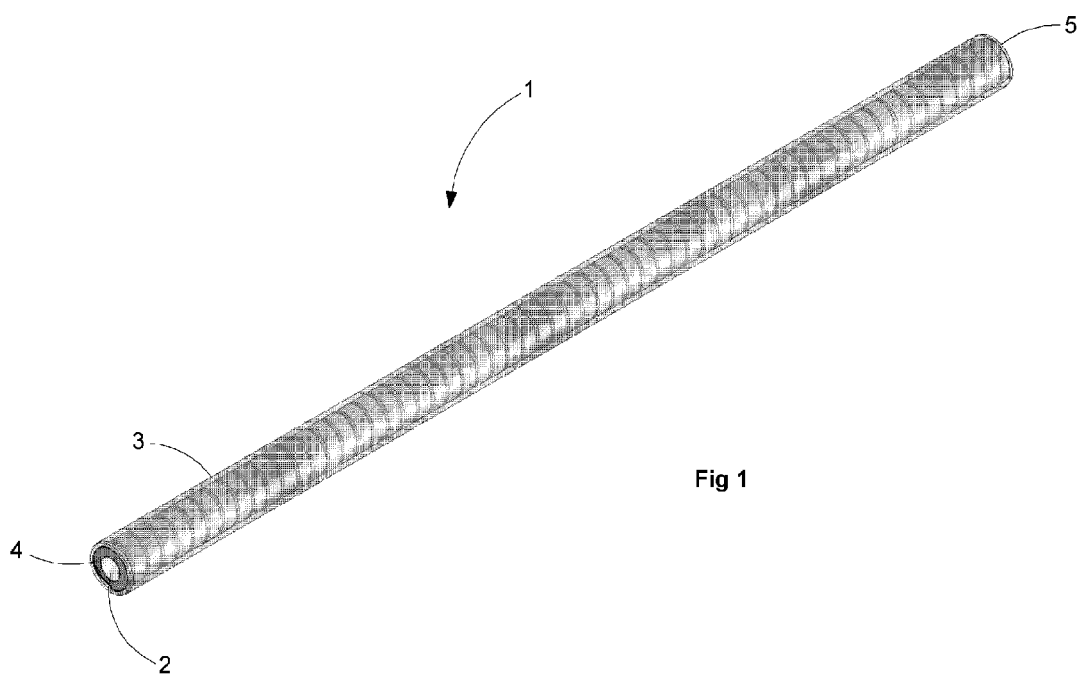
FIG. 1 is an isometric view of a molded spiral reinforced tubing according to embodiments of the present invention.
Figure 2:
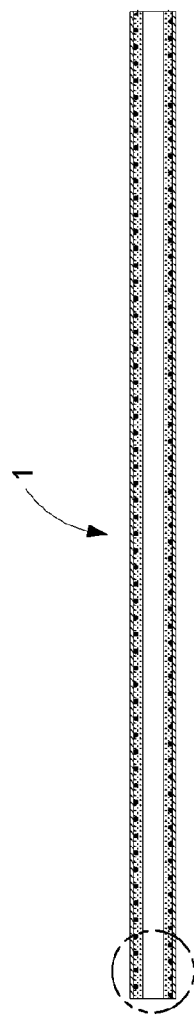
FIG. 2 is a cross-sectional view of the molded spiral reinforced tubing shown in FIG. 1.
Figure 2A:
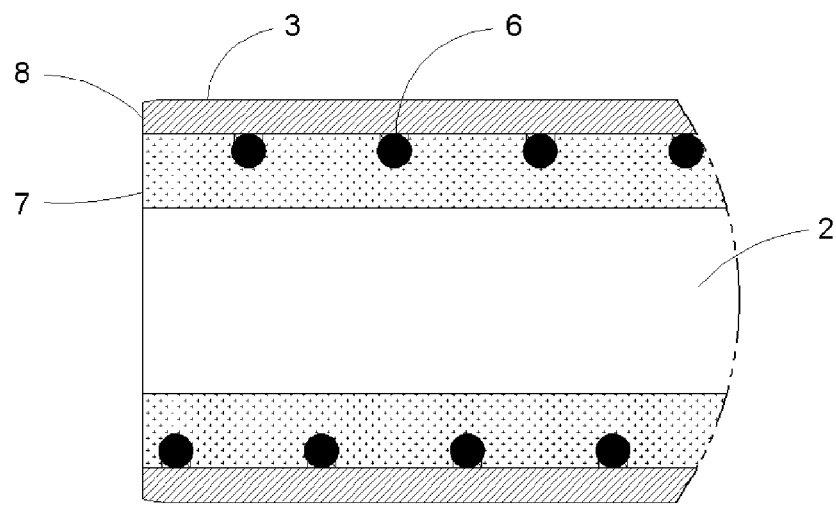
FIG. 2a is an enlarged view of a portion of the molded spiral reinforced tubing shown in FIGS. 1 and 2.

FIG. 1 depicts a reinforced tubing 1 according to embodiments of the present invention. FIG. 2 depicts a sectional view of the molded spiral reinforced tubing 1, and FIG. 2a is an enlarged view of a segment from FIG. 2 depicting a single spiral reinforcement member 6, an inner molded layer 7, and an outer molded layer 8. The tubing 1 includes a continuous lumen 2 and an outer surface 3 between tubing ends 4 and 5. As will be described in more detail herein, the tubing 1 is molded and includes a spiral reinforcement. It has utility in a variety of applications where flexible fluid conduit with spiral reinforcement improves performance characteristics by enhancing resistance to deformation from internal or external forces. In some applications, the reinforced tubing 1 may be used in medical devices, since the construction conforms with variations in the patient's anatomy. One example use for tubing 1 in a medical device is as a fluid conduit between components in the medical device. Examples of medical devices that might utilize reinforced tubing 1 as a fluid conduit between components are inflatable penile prostheses, inflatable mammary prostheses, inflatable urinary or fecal incontinence devices, inflatable tissue expanders, and devices utilizing implantable injection ports.

Figure 3:
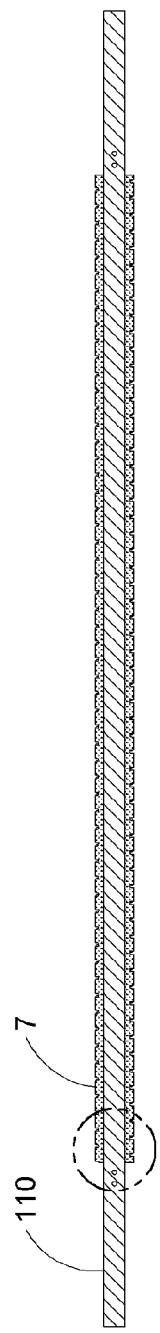
FIG. 3 is a cross-sectional view of a core and inner layer of the molded spiral reinforced tubing according to the present invention.
Figure 4:
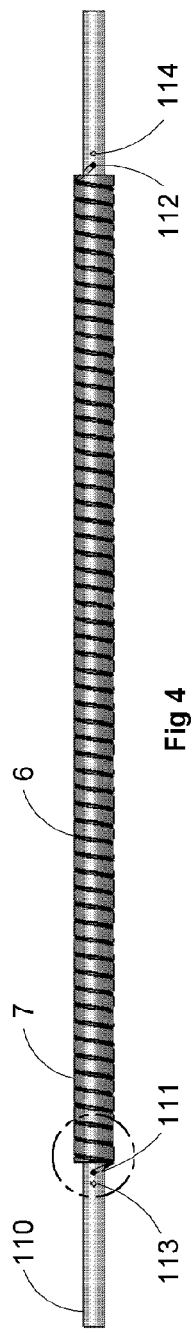
FIG. 4 is a plan view of the core and inner layer of the molded spiral reinforced tubing with a reinforcement member according to the present invention.
Figure 5:
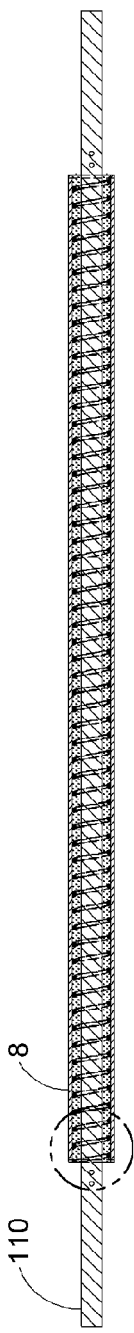
FIG. 5 is a cross-sectional view of the core and inner layer with an outer layer molded over the inner layer and the reinforcement member according to the present invention.
Figure 3A:
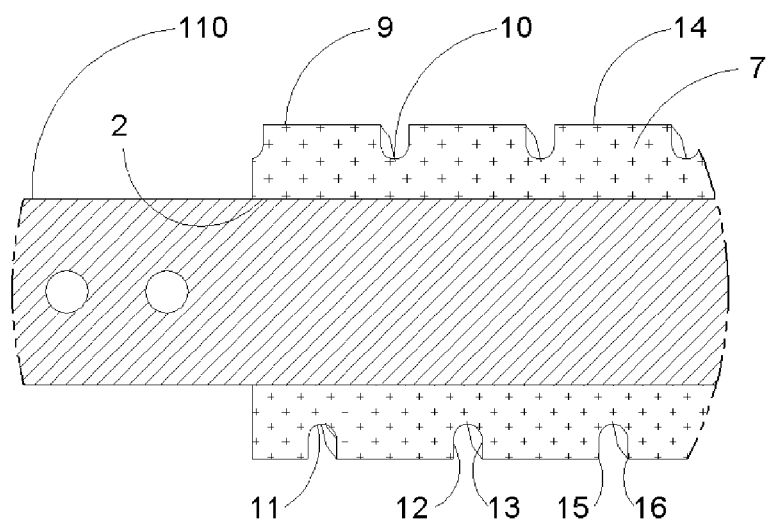
FIG. 3a is an enlarged cross-sectional view of the core and inner layer shown in FIG. 3.

FIGS. 3-5 illustrate steps in the formation of the spiral reinforced tubing 1 illustrated in FIGS. 1 and 2. FIG. 3 is a sectional view of a core 110 and the inner layer 7 of a molded spiral reinforced tubing 1. FIG. 3a is an enlarged view of the portion circled in FIG. 3 depicting the inner molded layer 7 including the lumen 2 (defined by the diameter of the core 110) and an outer surface 9. The outer surface 9 has a major diameter 14 and includes a recessed pathway 10 for receiving the continuous spiral reinforcement member 6 (not shown in FIGS. 3 and 3a). The pathway 10 includes arc 11 at its base (i.e., the portion of the pathway most proximate to the lumen 2). Surfaces 12 and 13 connect the arc 11 to the outer surface 9. A transition arc 15 may extend between the surface 12 and the outer surface 9, and a transition arc 16 may extend between the surface 13 and the outer surface 9. In some embodiments, the radius of the arc 11 is sized between about 2% and about 40% smaller than the radius of the reinforcement member 6, to retain the reinforcement member 6 in the pathway 10 between the surfaces 12 and 13. More preferably, the radius of the arc 11 is sized between about 10% and about 20% smaller than the radius of the reinforcement member 6. The depth of the pathway 10 (extending from the outer surface 9 to the bottom of the arc 11) is preferably equal to the diameter of the reinforcement member 6.

Figure 4A:
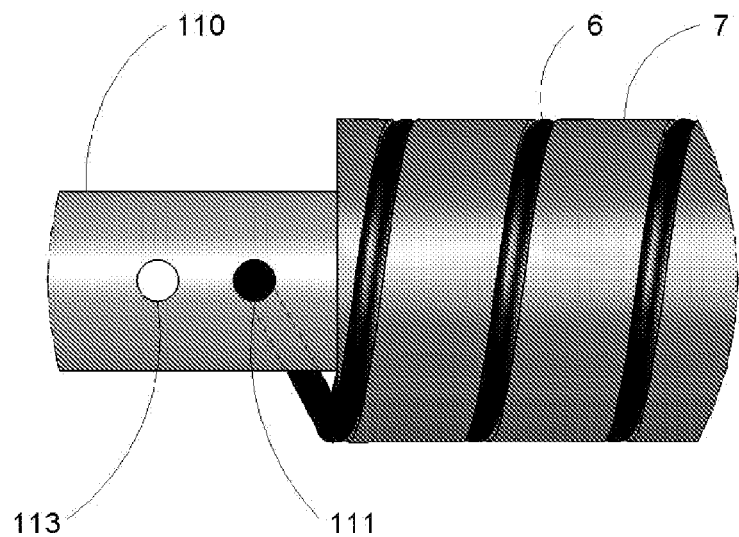
FIG. 4a is an enlarged plan view of the core and inner layer with the reinforcement member shown in FIG. 4.

FIG. 4 depicts the core 110 and the inner layer 7 of the spiral reinforced tubing 1 with the reinforcement member 6 secured to the core 110. FIG. 4a is an enlarged view of the portion circled in FIG. 4 depicting the inner molded layer 7 and the reinforcement member 6. The core 110 includes crossholes 111 and 112 formed proximate the ends of the core 110. The reinforcement member 6 is spirally wound and deposited into the recessed pathway 10. The ends of the reinforcement member 6 are inserted through the crossholes 111 and 112 of the core 110. The ends of the reinforcement member 6 are secured to the core 110 by mechanical means such as a knot, swedging, heading, or a retention cuff, or the reinforcement member 6 may be tucked between the core 110 and the inner layer 7. If the reinforcement member 6 is metallic in composition, swedging or heading may be accomplished mechanically. If the reinforcement member 6 is a thermoplastic composition, swedging or heading may be accomplished thermally. The core 110 may also have additional crossholes 113 and 114 to facilitate securement of the reinforcement member 6 to the core 110. The reinforcement member 6 is secured to the core 110 by first routing the reinforcement member 6 through the crosshole 111, then through the crosshole 113, then depositing the reinforcement into the recessed pathway 10, then routing the reinforcement through the crosshole 112, and finally through the crosshole 114. The crossholes 111-114 may penetrate the core 110 in the same or different radial orientations or may be angled so that the crosshole entry and exit may be at different elevations along the axis of the core 110 to ease installation of the reinforcement member 6. The crossholes 111-114 may be tapered to provide a larger opening or entry target to introduce the reinforcement member 6 and a smaller exit to retain the reinforcement member 6. The crossholes 111-114 may be electro-discharge machined (EDM) in the core 110, wherein the shape of each crosshole 111-114 is not limited to a uniform configuration as might be the case with twist drilling.

In some embodiments, the reinforcement member 6 has a diameter at least 0.002 inch smaller than the diameters of the crossholes 111 and 112. In one actual implementation, a 0.013-inch diameter Nylon 6 monofilament was utilized with a single 0.015-inch diameter crosshole on both ends of core 110.

The reinforcement member 6 forms a sharp bend as it transitions from the crosshole entry to overlying the circumference of the core 110 that provides a means to retain the reinforcement member 6 in the crosshole. Excess portions of the reinforcement member 6 may be trimmed flush with the exit side of the crossholes 111, 112.

Figure 5A:
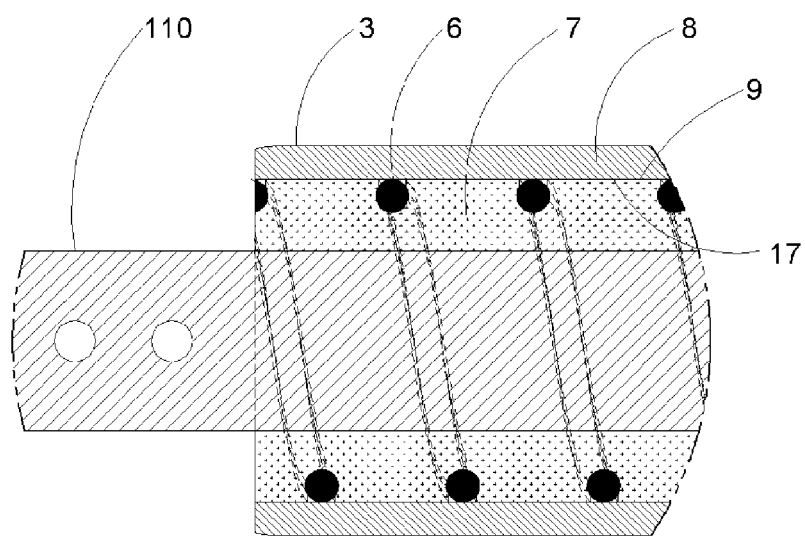
FIG. 5a is an enlarged cross-sectional view of the outer layer molded over the inner layer and the reinforcement member shown in FIG. 5.

FIG. 5 depicts a sectional view of the core 110 with the outer tubing layer 8 molded over the inner tubing layer 7 and the reinforcement member 6. FIG. 5a is an enlarged view of the portion circled from FIG. 5 depicting the outer molded layer 8 over the inner molded layer 7 and the reinforcement member 6. The outer molded layer 8 has an outer surface 3 and an inner surface 17. The inner surface 17 is conformal with the reinforcement member 6 and the outer surface 9 of the inner molded layer 7. In some embodiments, the outer molded layer 8 is chemically and mechanically bonded to inner molded layer 7, but not to the reinforcement member 6. Bonding of the molded layers 7 and 8 mechanically retains the reinforcement member 6 between the recessed pathway 10 of the inner layer 7 and the inner surface 17 of the outer layer 8. Materials selected for the outer layer 8 and the reinforcement member 6 prevent bonding of the outer layer 8 to the reinforcement member 6. If necessary, the reinforcement member 6 should be coated to prevent adhesion of the molded outer layer 8 to the reinforcement member 6. Additionally, the reinforcement member 6 may be coated to reduce the surface tension between the molded layers 7 and 8. The reinforcement member 6 should move freely in the recessed pathway 10 when the tubing is flexed, to prevent localized stresses that will reduce fatigue life.

Components of the spiral reinforced tubing 1 may be molded from a thermoplastic elastomer (e.g., polyurethane or polyvinyl chloride (PVC)), a thermoset elastomer (e.g., silicone or ethylene propylene diene monomer (EPDM)), or a combination of thermoplastic and thermoset elastomers. In certain implantable medical devices, such as implantable penile prostheses (IPP), silicone elastomer may be favored for its biocompatibility and low modulus. In these embodiments, the inner layer 7 is molded from a gum or high-consistency elastomer such as Nusil MED 4755, a platinum cured two-part elastomer. Two-part platinum elastomers have one part containing a catalyst that is mixed with the another part containing a crosslinker. Platinum cured two-part liquid injection molding (LIM) elastomer such as Nusil MED 4850 may also be used for the inner layer. High-consistency elastomers have good tear resistance, making them particularly suitable for the inner layer 7. The two parts of high consistency silicone elastomer are usually combined on a two-roll mill and molded using either compression or transfer molding methods. Alternatively, the inner layer 7 may be molded with one-part high-consistency elastomer, such as peroxide cured silicone elastomer, that may be compression or transfer molded.

The outer layer 8 may be molded from a gum or high-consistency elastomer such as Nusil MED 4755 because it has a high tear strength. The surface tension between the core 110 and the inner tubing layer 7 is configured to allow removal of the core 110 after molding, but also to minimize movement of the inner layer 7 on core 110 during overmolding of the outer layer 8. The selected overmolding parameters, such as mold temperature and transfer speed, optimize the elastomer flow over the reinforcement member 6 and inner layer 7.

The outer layer 8 may also be dispersion coated by dipping or spraying a dispersion grade elastomer. Dispersion grade elastomers can be formulated from peroxide, platinum or acetoxy cure silicone elastomers with a range of solids content using chemical solvents such as xylene, trichloroethane, naptha, hexane and toluene. Two part elastomers may be converted to dispersions prior to or after combining the two parts. Molding by dispersion coating is considerably slower than molding with gum or LIM elastomers using matched metal molds. The desired thickness of the outer layer 8 may be achieved with multiple dispersion coatings. Subsequent to volatilizing the dispersion solvent, the silicone elastomer is vulcanized. Acetoxy cured elastomers may also be used to provide improved abrasion resistance.

The reinforcement member 6 may be comprised of a metallic or polymeric material. Examples of metallic reinforcement are AISI 316L, a low carbon steel, or MP35N, a chromium, nickel, molybdenum and cobalt alloy. Metallic reinforcement has significantly higher tensile modulus than plastic reinforcement and can sustain permanent deformation if deformed beyond its elastic limit. The higher modulus metal reinforcement has less fatigue resistance than lower modulus plastic reinforcement. Metal reinforcements may be formed using spring winding equipment prior to placement on the inner layer 7.

Examples of polymeric materials suitable for reinforcement member 6 are nylon, polyester or polypropylene. Plastic reinforcement may be wound directly onto the tubing inner layer 7. For certain long-term medical applications, such as IPP, plastic reinforcement may better suited than metal, because it is less susceptible to permanent deformation, more resistant to fatigue and provides a more compliant tubing. In some embodiments, polyamide, commonly referred to as nylon, is favored for the reinforcement member 6 due its physical properties, biocompatibility, and because it is less likely to bond with the inner layer 7 during vulcanization.

Figure 6:
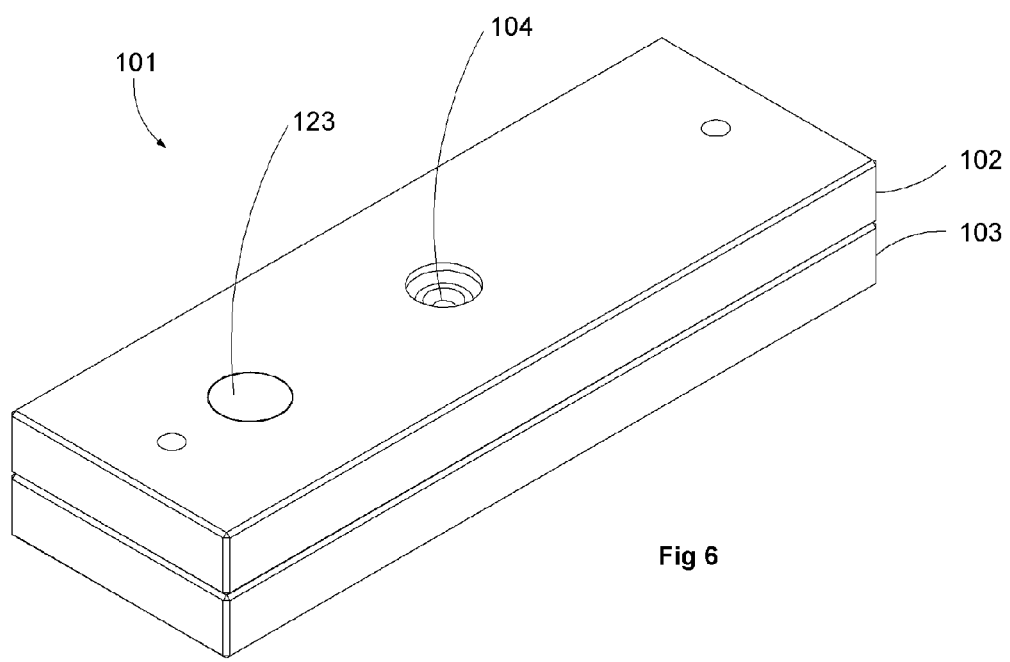
FIG. 6 is an isometric view of a transfer mold for molding inner and outer layers of a spiral reinforced tubing according to the present invention.

FIG. 6 depicts a family transfer mold 101 with cavity plates 102 and 103 in the closed mode. A sprue 104 is depicted in the center of the cavity plate 102. The family transfer mold 101 depicted in FIG. 6 is for molding a short length of molded spiral reinforced tubing 1 for developing test samples and prototypes. It will be appreciated that the cavity plates 102 and 103 can be sized to mold tubing 1 having a desired length. A rotary cavity shut off valve 123 in the cavity plate 102 allows for molding either the inner or outer layers separately or simultaneously. In actual implementation, production molds would likely be multi-cavity versions of either the inner layer 7 or the outer layer 8, since the inner layer 7 and the outer layer 8 may be molded from different elastomers or require different molding parameters such as transfer pressure, transfer speed, mold temperature and vulcanization or curing cycle times.

Figure 7:
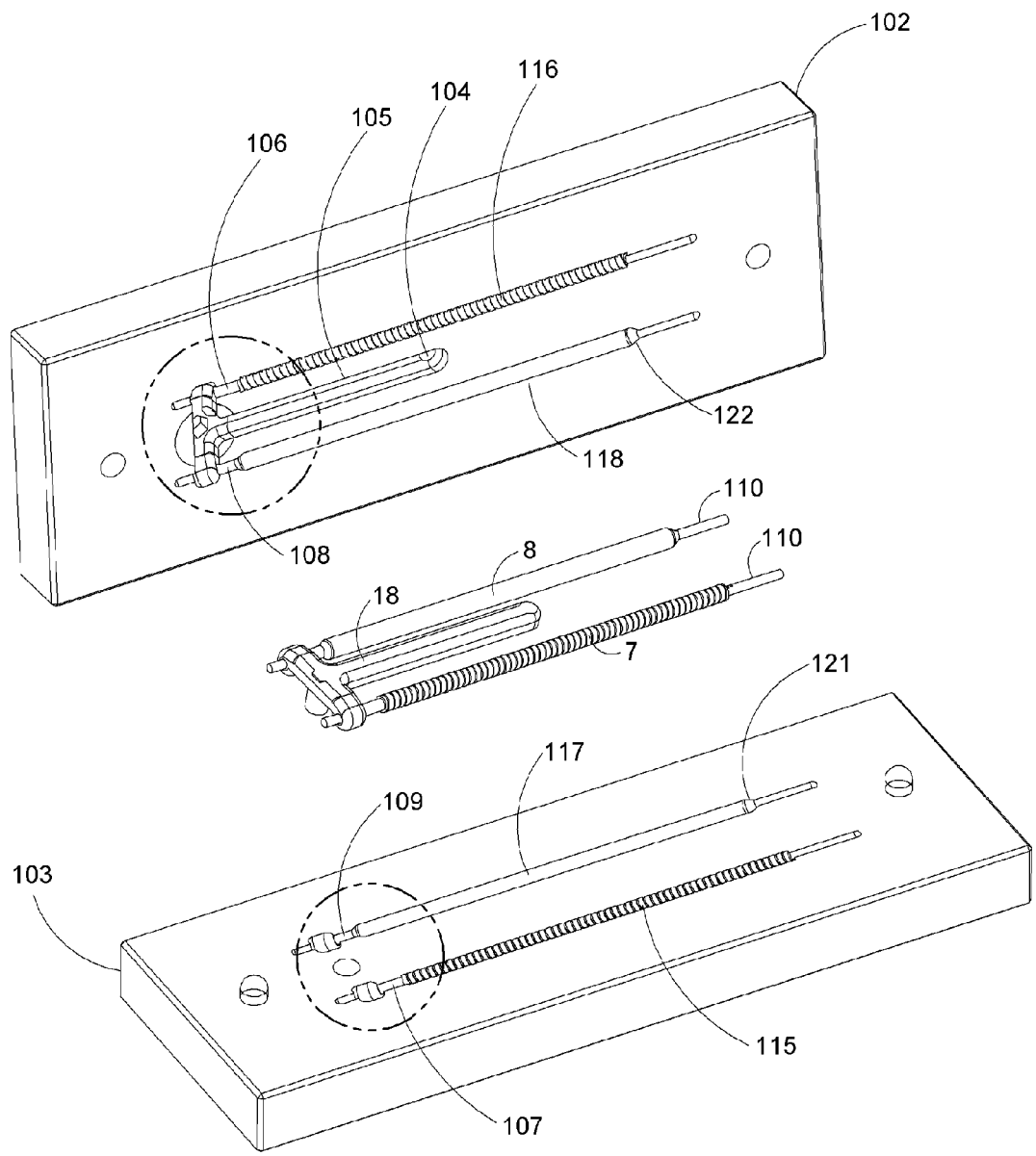
FIG. 7 is an isometric view of a transfer mold in an open arrangement showing the mold cavity halves and a molded shot with inner and outer tubing layers.

FIG. 7 depicts an isometric view of an opened family transfer mold 101 with the cavity plates 102 and 103 separated along their longitudinal axis for molding the inner layer 7 and the outer tubing layer 8. The cavity plate 102 includes a sprue 104 and a runner 105 for transferring elastomer to ring gate halves 106 and 108 in the cavity plate 102 and the opposing ring gate halves 107 and 109 located in the cavity plate 103. Ring gating from a single end of the tubing to introduce elastomer into the mold cavities substantially eliminates the potential for knit lines. Ring gating from a single end also minimizes the potential for bending of the mold core 110 that forms the lumen 2. FIG. 7 also depicts an inner layer cavity half 115 and an outer layer cavity half 117 in the cavity plate 103 and an inner layer cavity half 116 and an outer cavity half 118 in the cavity plate 102.

Figure 7B:
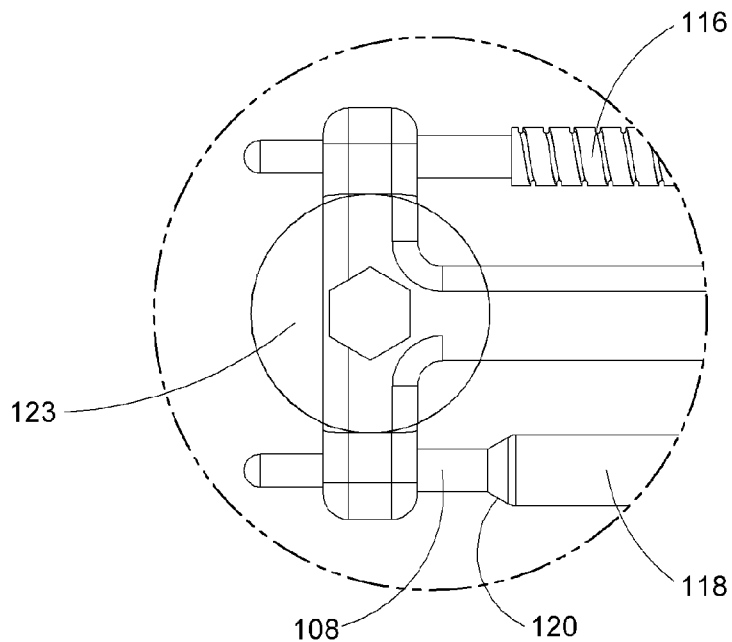
FIGS. 7a and 7b are enlarged plan views of portions of the mold cavity halves shown in FIG. 7.
Figure 7A:
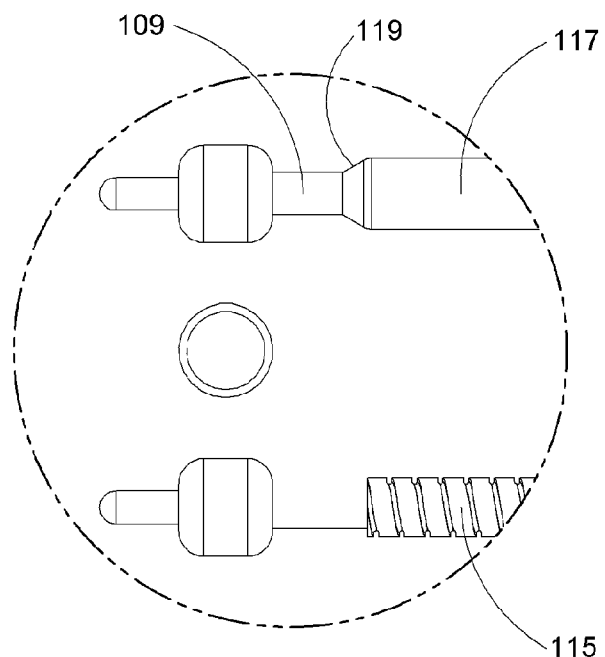

FIGS. 7a and 7b are enlarged plan views of the circled portions on the cavity plate 103 and the cavity plate 102, respectively, in FIG. 7. FIG. 7a is a plan view of the reinforcement securement surround half 119 located between the ring gate half 109 and the outer layer cavity half 117 in the cavity plate 103. FIG. 7b is a plan view of the reinforcement securement surround half 120 located between the ring gate half 108 and the outer layer cavity half 118 in the cavity plate 102. A reinforcement securement surround half 121 adjacent the outer layer cavity half 117 in cavity plate 103 and a reinforcement securement surround half 122 adjacent the outer layer cavity half 118 in cavity plate 102 are shown in FIG. 7. The reinforcement securement surrounds provide a segment to accommodate the bulk of the reinforcement securement means described above. FIG. 7 also shows a molded shot between separated cavity plates 102 and 103. The molded shot includes the inner layer 7 over the core 110, the outer tubing layer 8 over the inner tubing layer 7 and the reinforcement member 6, and a runner 18 connecting the cores 110.

The mold cavity plates 102 and 103 may be filled with a thermoset elastomer material using any suitable molding technique, such as compression, transfer, or LIM molding. With compression molding, the elastomer is placed in the mold cavities 115-118 and the elastomer is compressed as the mold is closed to fill out the part, replicating the mold detail. With transfer molding, the elastomer is placed in a transfer pot, usually a component of the press or mold. Transfer molding is accomplished by either closing the mold, if using a compression molding press, or closing the mold and activating the transfer plunger if using a transfer press. In either case, the elastomer is transferred through the sprue 104 in the mold and subsequently through the ring gate 106-109 to fill the mold forming the part. The runner 105 may be used to connect the sprue 104 and the gate 106-109. With LIM molding, multiple components of liquid elastomer are pumped separately to a mixing chamber from which they are fed into an injection chamber. The injection molding press closes the mold cavity plates 102 and 103 and subsequently injects the combined multi-component elastomer into the mold cavities 115-118, filling out the part. For thermoset elastomers, the parts may be compression, transfer or injection molded by introducing uncured elastomer into the mold cavities 115-118, thermally curing the elastomer for a specific time, opening the mold, and removing the part along with the sprue 104 and runner 105. For any thermoplastic elastomer, the parts may be injection molded by introducing molten elastomer into the mold cavities 115-118, thermally cooling the elastomer for a specific time, opening the mold, and removing the part along with the sprue 104 and runner 105.

FIG. 8 is a cross-sectional view of a single molded shot including the molded inner layer 7 on the core 110, the outer layer 8 molded over the inner layer 7 and the reinforcement member 6, and the runner 18 connecting cores 110. FIG. 8a is an enlarged cross-sectional view of the portion circled of the inner layer 7 on the core 110 in FIG. 8 depicting the ring gate 19. FIG. 8b is an enlarged cross-sectional view of the portion circled of the outer layer 8 on the core 110 in FIG. 8, depicting the ring gate 20 and the reinforcement securement surround 21.

While the present invention has been described with regard to a reinforced tubing 1 including a single spiral reinforcement member 6, it will be appreciated that variations on this design are contemplated. For example, in an alternative embodiment, the tubing 1 may be configured to accommodate a plurality of continuous spiral reinforcement members 6. Multiple spiral reinforcement members 6 may have advantages in certain applications and may be accomplished by providing detail for multiple reinforcement pathways 10 in the inner layer cavity halves 115 and 116, additional crossholes in the core 110, multiple recessed pathways 10 in the inner layer 7 and multiple reinforcement members 6 in the molded spiral reinforced tubing 1. Multiple reinforcement members 6 may be used, for example, to reduce the reinforcement angle with respect to the longitudinal axis of the tubing 1. Multiple reinforcement members 6 provide a larger reinforcement angle with respect to the tubing axis and will facilitate greater radial expansion of the lumen 2 for applications involving insertion of a connector or tubing insert.

In alternative embodiments, the reinforced tubing 1 is assembled with elements that provide additional functional components in the tubing 1. For example, in embodiments including multiple recessed pathways 10, a color coding member may be formed in one of the recessed pathways 10 to color code the tubing 1 for identification for particular applications. As another example, one or more of the multiple recessed pathways 10 may have one or more electrically conductive paths formed therein to communicate electrical signals between components connected by the tubing 1. One or more of the multiple recessed pathways 10 may also include a fiber optic element to facilitate optical communication across the tubing 1. Furthermore, one or more of the multiple recessed pathways 10 may have a sensing element formed therein to sense physiological characteristics (e.g., oxygen or pH levels) around the tubing 1.

Figure 9:
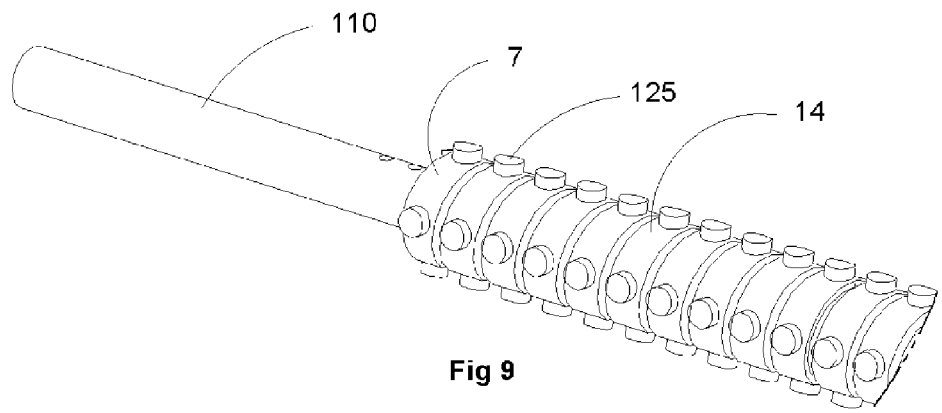
FIG. 9 is an isometric view of a molded inner layer on the mold core, with multiple centering projections emanating from the outer surface of the inner molded layer according to embodiments of the present invention.
Figure 9A:
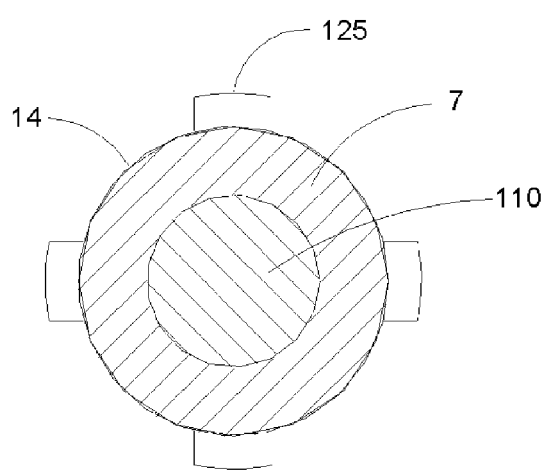
FIG. 9a is a cross-sectional view of the molded inner layer on the mold core shown in FIG. 9.

FIG. 9 depicts inner layer 7 on the core 110 with multiple centering projections 125 emanating from the outer surface 14 of the inner layer 7, according to an alternative embodiment of the present invention. FIG. 9a is an enlarged view of a cross-section of the inner layer 7 and the core 110 shown in FIG. 9 depicting multiple centering projections 125 emanating from the major diameter 14 of the inner layer 7. The embodiment shown in FIGS. 9 and 9a is configured to center the inner layer 7 with respect to the outer layer mold cavities 117 and 118 during molding of the outer layer 8. In particular, the centering projections 125 are configured to contact the outer layer mold cavity halves 117 and 118, during molding of the outer molded layer 8, to facilitate centering of inner molded tubing layer 7 within outer molded tubing layer 8. In some embodiments, the centering projections 125 are positioned at a minimum of 120° apart radially, and a suitable distance apart axially, to maintain centering with respect to the mold cavity halves 117 and 118.

Figure 10:
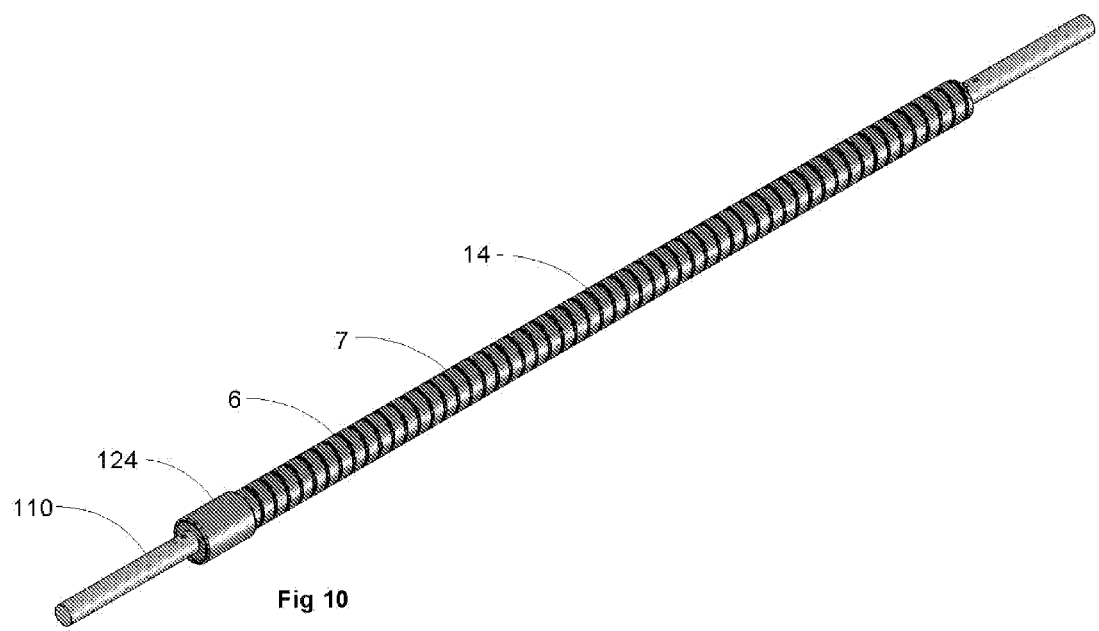
FIG. 10 is an isometric view of a molded inner layer and reinforcement on a mold core, with a centering sleeve installed over the outer surface of the inner molded layer according to embodiments of the present invention.
Figure 11:
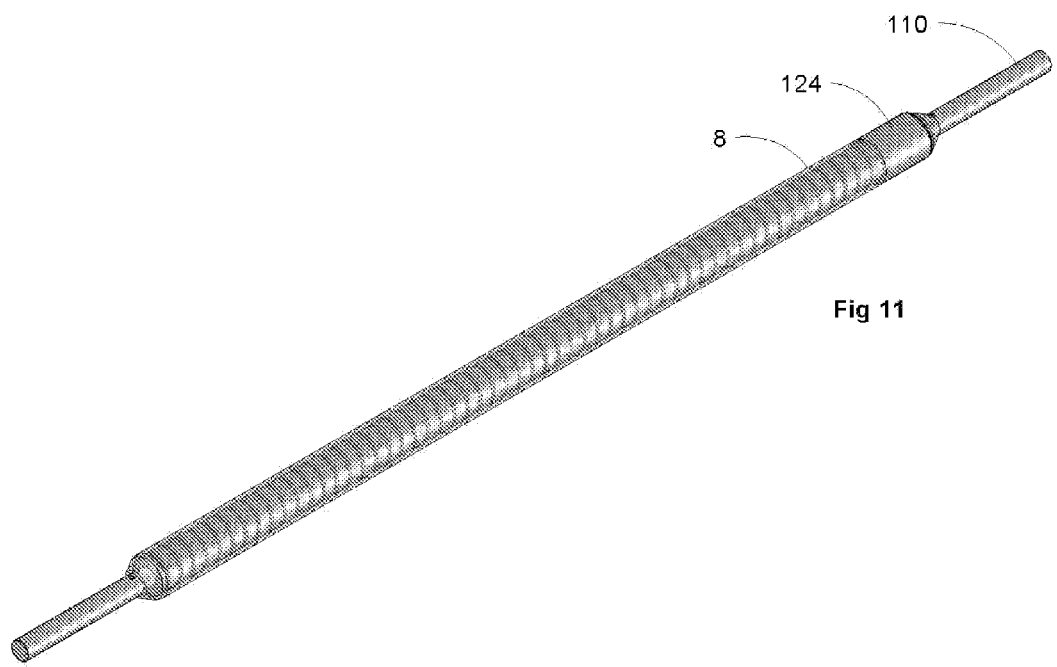
FIG. 11 is an isometric view of molded spiral reinforced tubing with the centering sleeve on the mold core after molding the outer layer.

The centering projections 125 is just one example mechanism that may be used to center the inner layer 7 with respect to the outer layer mold cavities 117 and 118 during overmolding. For example, FIG. 10 depicts the inner layer 7 and the reinforcement member 6 on the core 110 and a centering sleeve 124 positioned over the outer surface 14 of the inner layer 7 and the reinforcement member 6, according to another embodiment of the present invention. The centering sleeve 124 is disposed around the outer surface 14 of the inner layer 7 and centers the inner layer 7 and the reinforcement member 6 within outer molded tubing layer 8, during molding of the outer layer 8. In some embodiments, the diameter of the bore of centering sleeve 124 is sized 0.001 to 0.002 inch greater than the diameter of the outer surface 14 of the inner layer 7 and the outer radius of the centering sleeve 124 is sized 0.001 to 0.002 inch smaller than the radii of the outer layer cavity halves 117 and 118. The centering sleeve 124 is placed over the inner layer 7 and the reinforcement member 6 and axially located proximal to outer layer ring gate halves 108 and 109. As elastomer is introduced into the mold, it advances the centering sleeve 124 axially between inner molded tubing layer 7 and cavity halves 117 and 118 until the elastomer flow is complete and the centering sleeve 124 is distal to the ring gate 108, 109. The centering sleeve 124 can be fabricated from a heat resistant plastic such as polysulfone or metal such as aluminum or stainless steel. FIG. 11 depicts molded spiral reinforced tubing with the outer layer 8 and the centering sleeve 124 on the mold core 110 after molding the outer layer 8.

Figure 12:
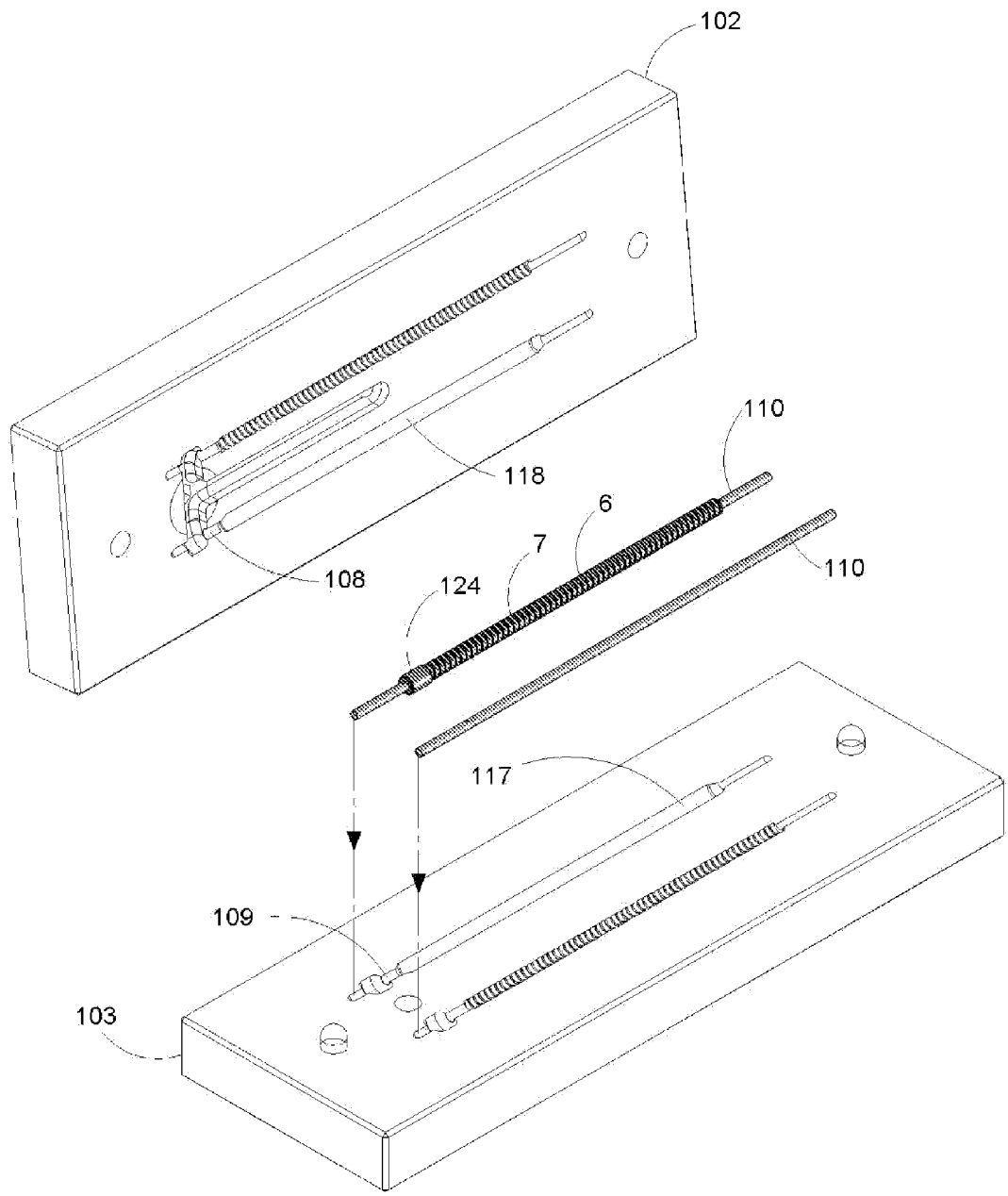
FIG. 12 is an isometric view of a transfer mold for molding inner and outer layers of a molded spiral reinforced tubing, depicting axial orientation of the centering sleeve over inner layer prior to molding.
Figure 13:
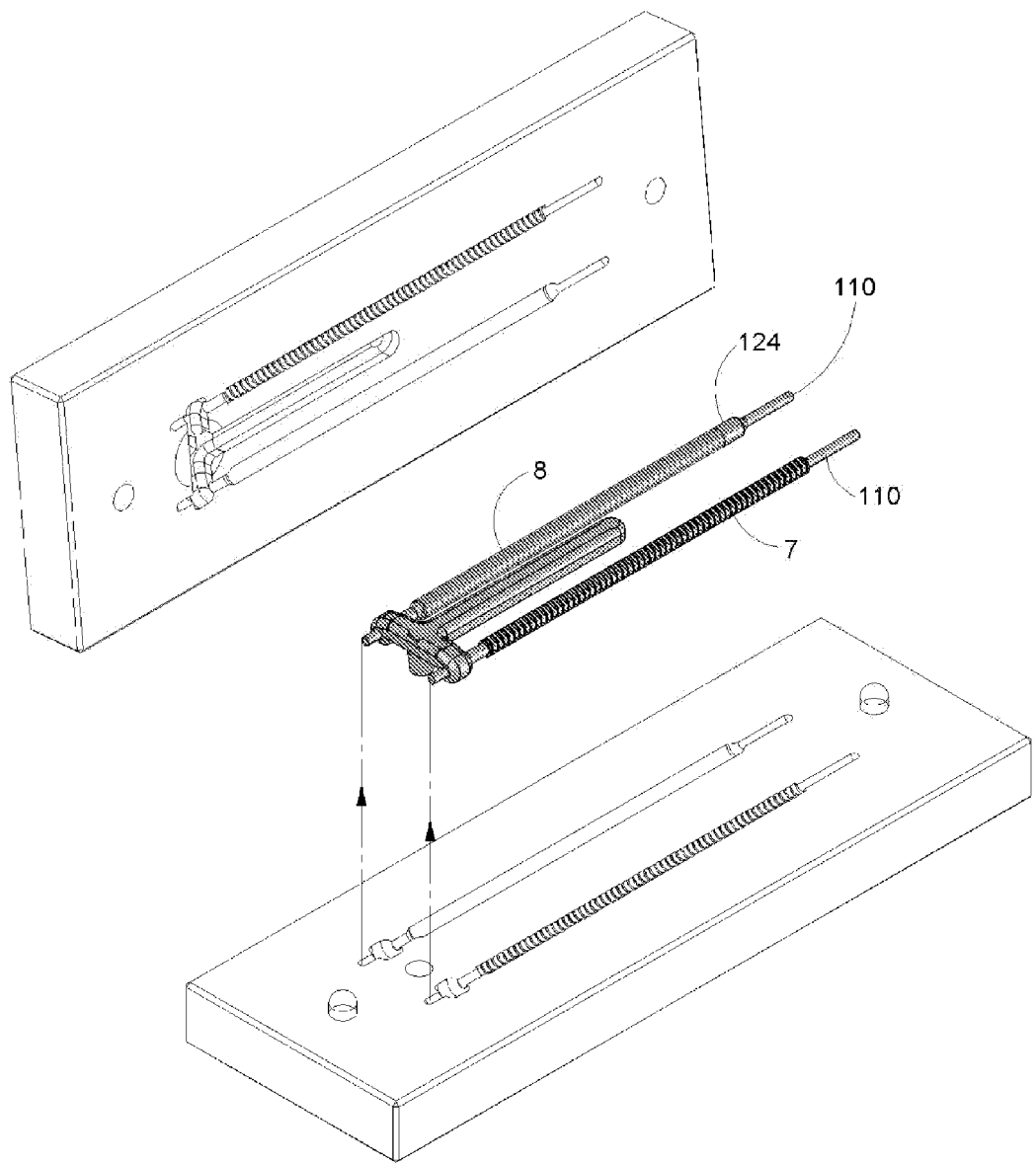
FIG. 13 is an isometric view of a transfer mold for molding inner and outer layers of a molded spiral reinforced tubing, depicting axial orientation of the centering sleeve after molding.

FIG. 12 is an isometric view of a family transfer mold for molding the inner layer 7 and the outer layer 8, prior to molding the device shown in FIGS. 10 and 11. The cavity plates 102 and 103 are separated along their longitudinal axis. The centering sleeve 124 is located proximal to the ring gate half 108 of the cavity plate 102 and the ring gate half 109 of the cavity plate 103 prior to molding. The centering sleeve 124 is radially positioned over the inner layer 7 and the reinforcement member 6 on the core 110. FIG. 13 is an isometric view of a family transfer mold after molding the inner layer 7 on the core 110 and the outer layer 8 over the inner layer 7 and the reinforcement member 6. As is shown, the centering sleeve 124 travels to the end distal to the ring gate 108, 109 during molding of the outer layer 8.

Molded tubing provides design opportunity because the bore and major diameter need not have a continuous profile. Molding multiple layer tubing provides additional design freedom especially when reinforcement is incorporated in the tubing. For example, the tubing 1 of the present invention has a non-continuous outer surface 14 on the inner layer 7 that includes a recessed pathway 10 for accommodating a spiral reinforcement member 6. The recessed pathway 10 eliminates the need to tension the reinforcement member 6 to stabilize it during subsequent manufacturing operations, which also provides design opportunity to fabricate tubing 1 with a continuous lumen 2. A reinforcement member 6 that is not tensioned is less likely to cause localized stress that could initiate fatigue failure than a tensioned reinforcement. In addition, the greatest elongation during bending or flexing of the inner layer of the tubing 1 is directed to the thinnest cross-section at the bottom of the recessed pathway 10. The compressive and tensile stresses from flex of the tubing 1 are minimized by reducing the thickness. Spiral reinforcement member 6 causes the greatest abrasive activity at the base of the recessed pathway during flex of the tubing 1. However, the reduction or elimination of tension on the reinforcement member 6 as is done in the tubing 1 according to the present invention can significantly reduce this abrasive activity. That is, the tubing 1 is provided with the recessed pathway 10 on the inner layer 7, facilitating spiral reinforcement with minimal or no tension, so that compressive forces caused by the reinforcement member 6 on the adjacent inner layer 7 during flex of tubing 1 are reduced for greater fatigue resistance.

One or more of the following advantages may be provided in certain implementations. First, molded spiral reinforced tubing can be provided that is simple to manufacture. Second, molded spiral reinforced tubing can be provided that can be manufactured more consistently than extruded spiral reinforced tubing. Third, molded tubing provides greater design freedom over extruded tubing because the tubing profile need not be continuous and enables incorporation of features for ease of manufacture or improved performance. Fourth, molded spiral reinforced tubing can be provided with a constant lumen without undulations from tensioned reinforcement. Fifth, molded spiral reinforced tubing can be provided with greater fatigue resistance than extruded spiral reinforced tubing.

A significant advantage in molded silicone tubing over extruded silicone tubing is that molded tubing is compressed and densified during vulcanization or curing. Extruding tubing is compressed as it is forced through an extrusion die but is not densified during vulcanization. Physical properties are enhanced as the interface between the elastomer and reinforcing filler improves and mechanical densification that occurs during closed molding improves that interface.

What is claimed is:

1. A method for manufacturing a tubing for connecting components in medical devices, the method comprising:
    transfer or injection molding an inner layer around a core to define an inner surface adjacent to the core and an outer surface opposite the inner surface using inner layer cavity mold halves, said outer surface including one or more recessed pathways defined therein;
    forming a reinforcement member in each of the one or more recessed pathways of the molded inner layer;
    transfer or injection molding an outer layer including an inner surface and an outer surface over the inner layer and the reinforcement member using outer layer cavity mold halves, wherein the inner surface of the outer layer substantially conforms to the outer surface of the inner layer and the reinforcement member, at least one of the inner layer cavity mold halves and the outer layer cavity mold halves including a sprue and a runner for transferring an elastomer to ring gate halves on an end of the tubing that introduces the elastomer into a mold cavity;
    removing the outer layer, inner layer, and reinforcement member from the outer layer mold cavity halves; and
    removing the core from within the inner layer to provide a lumen through the inner layer.

2. The method of claim 1, wherein the mold cavity halves are separatable along a longitudinal axis of the mold cavity halves.

3. The method of claim 1, wherein the core has a first end and a second end and is retained at said first and second ends by the mold cavity halves when molding the inner layer and the outer layer.

4. The method of claim 1, wherein the mold cavity halves include a means of temperature control.

5. The method of claim 1, wherein, prior to molding the outer layer, the method further comprises:
    securing a centering sleeve around the inner layer and reinforcement member proximate the ring gate that advances axially during molding of the outer layer, wherein the centering sleeve substantially centers the inner layer and the outer layer with respect to a common longitudinal axis.

6. The method of claim 1, wherein the inner layer is molded with a plurality of projections extending radially from the outer surface of the inner layer, and wherein the projections are configured to contact surfaces of the mold cavity halves for the outer layer to substantially center the inner layer and the outer layer with respect to a common longitudinal axis.

7. The method of claim 1, wherein the mold cavity halves for the inner layer include an electro-discharge machined (EDM) surface that is imprinted on the outer surface of the molded inner layer to promote mechanical adhesion of the outer layer to the inner layer.

8. The method of claim 1, wherein the reinforcement member is retained by the core while molding the outer layer.

9. The method of claim 8, wherein the core has a first end and a second end opposite the first end and includes at least one crosshole through the core proximate each of said first and second ends of the core to retain the reinforcement member.

10. A method for manufacturing a tubing for connecting components in medical devices, the method comprising:
    transfer or injection molding an inner layer with a recessed pathway over a core in inner layer mold cavity halves;
    removing the molded inner layer and core from the inner layer mold cavity halves;
    forming a reinforcement member in the recessed pathway of the inner layer, said reinforcement member having a first end and a second end;
    securing said first and second ends of the reinforcement member to the core;
    transfer or injection molding an outer layer over the inner layer and the reinforcement member in outer layer mold cavity halves, at least one of the inner layer cavity mold halves and the outer layer cavity mold halves including a sprue and a runner for transferring an elastomer to ring gate halves on an end of the tubing that introduces the elastomer into a mold cavity;
    removing the outer layer, inner layer, and reinforcement member from the outer layer mold cavity halves; and
    removing the core from within the inner layer to provide a lumen through the inner layer.

11. The method of claim 10, wherein each of the inner layer mold cavity halves and outer layer mold cavity halves are separable along a longitudinal axis of the mold cavity halves.

12. The method of claim 10, wherein the core has a first end and a second end and is retained at said first and second ends by the mold cavity halves when molding the inner layer and the outer layer.

13. The method of claim 10, wherein, prior to molding the outer layer, the method further comprises:
    securing a centering sleeve around the inner layer and reinforcement member proximate the ring gate that advances axially during molding of the outer layer to substantially center the inner layer and the outer layer with respect to a common axis.

14. The method of claim 10, wherein the inner layer is molded with a plurality of projections extending radially from the outer surface of the inner layer, and wherein the projections are configured to contact surfaces of the outer layer mold cavity halves to substantially center the inner layer and the outer layer with respect to a common axis.

15. The method of claim 10, wherein the inner layer mold cavity halves include an electro-discharge machined (EDM) surface that is imprinted on the outer surface of the inner layer to promote mechanical adhesion of the outer layer to the inner layer.

16. The method of claim 10, wherein the core has a first end and a second end opposite the first end and includes at least one crosshole through the core proximate each of said first and second ends of the core to secure the reinforcement member to the core.

* * * * *